(12) United States Patent
Röttger et al.

(10) Patent No.: US 7,030,286 B2
(45) Date of Patent: Apr. 18, 2006

(54) METHOD FOR PRODUCING 1-OCTENE

(75) Inventors: Dirk Röttger, Recklinghausen (DE); Axel Tuchlenski, Muelheim (DE)

(73) Assignee: OXENO Olefinchemie GmbH, Marl (DE)

( * ) Notice: Subject to any disclaimer, the term of this patent is extended or adjusted under 35 U.S.C. 154(b) by 320 days.

(21) Appl. No.: 10/470,280

(22) PCT Filed: Jan. 18, 2002

(86) PCT No.: PCT/EP02/00455

§ 371 (c)(1),
(2), (4) Date: Aug. 8, 2003

(87) PCT Pub. No.: WO02/062732

PCT Pub. Date: Aug. 15, 2002

(65) Prior Publication Data

US 2004/0059170 A1    Mar. 25, 2004

(30) Foreign Application Priority Data

Feb. 8, 2001   (DE) ................................ 101 05 751

(51) Int. Cl.
*C07C 2/24*      (2006.01)
(52) U.S. Cl. ...................... 585/514; 585/510; 585/520; 585/527; 585/531
(58) Field of Classification Search ................ 585/510, 585/514, 520, 527, 531
See application file for complete search history.

(56) References Cited

U.S. PATENT DOCUMENTS

| 5,254,782 | A  | * | 10/1993 | Schaart et al. ............... 585/509 |
| 6,627,782 | B1 |   | 9/2003  | Kaizik et al. |
| 2004/0242947 | A1 |   | 12/2004 | Beller et al. |
| 2005/0038273 | A1 |   | 2/2005  | Rottger et al. |
| 2005/0065387 | A1 |   | 3/2005  | Beller et al. |

FOREIGN PATENT DOCUMENTS

WO    92 10450    6/1992

OTHER PUBLICATIONS

U.S. Appl. No. 10/538,475, filed Jun. 7, 2005, Kaizik et al.
U.S. Appl. No. 10/538,359, filed Jun. 13, 2005, Rottger et al.
U.S. Appl. No. 10/517,620, filed Dec. 23, 2004, Rottger et al.

* cited by examiner

*Primary Examiner*—Walter D. Griffin
*Assistant Examiner*—In Suk Bullock
(74) *Attorney, Agent, or Firm*—Oblon, Spivak, McClelland, Maier & Neustadt, P.C.

(57) ABSTRACT

The invention relates to a process for preparing 1-octene by reacting 1,3-butadiene with a telogen of the formula H—X—Y—H, where X is O, N, S or P and Y is C, N or Si and X and Y bear, depending on their valence, further substituents, in the presence of a telomerization catalyst to form a telomer of the formula $H_2C=CH-CH_2-CH_2-CH_2-CH=CH-CH_2-X-Y-H$, partially hydrogenating the telomer to form a 1-substituted 2-octene of the formula $H_3C-CH_2-CH_2-CH_2-CH_2-CH=CH-CH_2-X-Y-H$ and dissociating the 1-substituted 2-octene to give 1-octene.

31 Claims, No Drawings

METHOD FOR PRODUCING 1-OCTENE

BACKGROUND OF THE INVENTION

The invention relates to a process for preparing 1-octene by telomerization of 1,3-butadiene by means of a telogen in the presence of a telomerization catalyst, partial hydrogenation of the telomer and dissociation of the hydrogenated intermediate.

DESCRIPTION OF THE BACKGROUND

1-Octene is used in large quantities in the production of various chemical products. For example, surface-active substances, plasticizers, lubricants and polymers are produced from 1-octene. Another large field of application is its use as comonomer in polymers, especially in polyethylene.

Virtually all processes which are at present utilized commercially for the production of 1-octene are based on ethene as raw material. Ethene is oligomerized to give a range of α-olefins as main products. With appropriate choice of catalyst and process conditions, the amount of 1-octene in the product can be optimized and is then about 25%. Apart from these processes, by means of which most 1-octene is produced, the isolation of 1-octene from the product mixture from the Fischer-Tropsch reaction has attained some importance.

Apart from ethene-based processes, processes which use 1,3-butadiene as raw material are also known from the literature. However, 1-octene is not obtainable directly, for example by means of a dimerization, from butadiene, but is obtained after a plurality of process steps. Thus, WO 92/10450 describes a process in which 1,3-butadiene is reacted with, preferably, methanol or ethanol to form a 2,7-octadienyl ether which, after hydrogenation to the octyl ether, is dissociated to give 1-octene. An analogous route is employed in EP-A-0 440 995, but the reaction in the first step is with a carboxylic acid. The processes both involve an analogous first process step which is generally referred to as telomerization. In the telomerization, a telogen (in EP-A-0 440 995, the carboxylic acid) is generally reacted with a taxogen (1,3-butadiene, 2 equivalents) to form a telomer.

Examples of telomerization reactions are described in, inter alia, E. J. Smutny, J. Am. Chem. Soc. 1967, 89, 6793; S. Takahashi, T. Shibano, N. Hagihara, Tetrahedron Lett. 1967, 2451; EP-A-0 561 779, U.S. Pat. Nos. 3,499,042, 3,530,187, GB 1 178 812, NL 6 816 008, GB 1 248 593, U.S. Pat. Nos. 3,670,029, 3,670,032, 3,769,352, 3,887,627, GB 1 354 507, DE 20 40 708, U.S. Pat. Nos. 4,142,060, 4,146,738, 4,196,135, GB 1 535 718, U.S. Pat. No. 4,104,471, DE 21 61 750 and EP-A-0 218 100.

In the butadiene-based processes for preparing 1-octene, as described, for example, in WO 92/10450 or EP-A-0 440 995, the 1-octene is obtained by dis-sociation of an n-octane substituted in the 1 position. The selectivities in this step are often unsatisfactory. Thus, WO 92/10450 reports the selectivity to octenes in the dissociation of 1-methoxyoctane at a conversion of 80% as being 66%.

SUMMARY OF THE INVENTION

It is therefore an object of the invention to discover a process by means of which 1-octene can be prepared from 1,3-butadiene but which circumvents the abovementioned dissociation step.

It has now been found that 1-octene can be prepared in high purity and good yield by a process which is made up essentially of three steps.

The invention accordingly provides a process for preparing 1-octene by
1) reacting 1,3-butadiene with a telogen of the formula I,

where X is O, N, S or P and Y is C, N or Si and X and Y may, depending on the valence of X and Y, bear further substituents, in the presence of a telomerization catalyst to form a telomer of the formula II

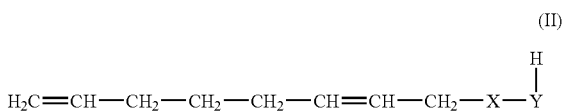

where X and Y are as defined above,
2) partially hydrogenating the compound of the formula II to form a compound of the formula III,

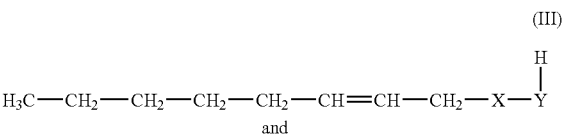

3) obtaining 1-octene by dissociation of the compound of the formula III.

DETAILED DESCRIPTION OF THE PREFERRED EMBODIMENTS

In the telomerization in step 1) of the process of the present invention, it is possible to use either pure 1,3-butadiene or mixtures in which 1,3-butadiene is present. As 1,3-butadiene-containing mixtures, preference is given to using mixtures of 1,3-butadiene with other $C_4$-hydrocarbons. Such mixtures are obtained, for example, in cracking processes for the production of ethene in which refinery gases, naphtha, gas oil, LPG (liquefied petroleum gas), NGL (natural gas liquid), etc., are reacted. The $C_4$ fractions obtained as by-product in these processes comprise variable amounts of 1,3-butadiene, depending on the cracking process. Typical 1,3-butadiene concentrations in the $C_4$ fraction obtained from a naphtha steam cracker are 20–70% of 1,3-butadiene.

The $C_4$ components n-butane, i-butane, 1-butene, cis-2-butene, trans-2-butene and i-butene which are likewise present in these fractions do not interfere, or do not interfere significantly, in the reaction in the telomerization step. On the other hand, dienes having cumulated double bonds (1,2-butadiene, allene, etc.) and alkynes, in particular vinylacetylene, act as moderators in the telomerization reaction. It is therefore advantageous to remove the $C_4$-alkynes and if necessary the 1,2-butadiene beforehand. This may, if possible, be carried out by physical methods such as distillation or extraction. Possible chemical routes are selective hydrogenation of the alkynes to alkenes or alkanes and reduction of the cumulated dienes to monoenes. Processes for such hydrogenations are described in the prior art, for example in WO 98/12160, EP-A-0 273 900, DE-A-37 44 086 or U.S. Pat. No. 4,704,492.

As telogens in step 1 of the process of the invention, it is possible to use all compounds which have the formula I. In the formula I, X is O, N, S or P and Y is C, N or Si, where X and Y may, depending on the valence of X and Y, bear further substituents. Preferred substituents on X and Y are hydrogen, alkyl radicals having 1–50 carbon atoms, aryl radicals having 6–50 carbon atoms and/or heteroaryl radicals, where the substituents may be identical or different and may in turn be substituted by the groups alkyl, aryl, —F, —Cl, —Br, —I, —$CF_3$, —OR, —COR, —$CO_2R$, —OCOR, —SR, —$SO_2R$, —SOR, —$SO_3R$, —$SO_2NR_2$, —$NR_2$, —N=$CR_2$, —$NH_2$ where R=H or a substituted or unsubstituted, aliphatic or aromatic hydrocarbon radical having from 1 to 25 carbon atoms. Preference is given to X being O or N and Y being C.

Specific examples of telogens of the formula I are
monoalcohols such as methanol, ethanol, n-propanol, isopropanol, allyl alcohol, n-butanol, i-butanol, octanol, 2-ethylhexanol, isononanol, benzyl alcohol, cyclohexanol, cyclopentanol or 2,7-octadien-1-ol,
dialcohols such as ethylene glycol, 1,2-propane-diol, 1,3-propanediol, 1,4-butanediol, 1,2-butanediol, 2,3-butanediol and 1,3-butanediol,
hydroxy compounds such as α-hydroxyacetic esters,
primary amines such as methylamine, ethylamine, propylamine, butylamine, octylamine, 2,7-octadienylamine, dodecylamine, ethylenediamine or hexamethylenediamine,
secondary amines such as dimethylamine, diethyl-amine, N-methylaniline, bis(2,7-octadienyl)amine, dicyclohexylamine, methylcyclohexylamine, pyrrolidine, piperidine, morpholine, piperazine or hexamethylenimine.

Telogens which can themselves be obtained via a telomerization reaction can be used directly or else can be formed in situ. Thus, for example, 2,7-octadien-1-ol can be formed in situ from water and butadiene in the presence of the telomerization catalyst, 2,7-octadienylamine can be formed from ammonia and 1,3-butadiene, etc.

Telogens which are particularly preferably used are methanol, ethanol, n-butanol, ethylene glycol, 1,3-propanediol, dimethylamine and diethylamine. Very particular preference is given to using methanol.

To determine the ratio of telogen to 1,3-butadiene in the telomerization reaction, the number of active hydrogen atoms in the telogen has to be taken into account. Thus, for example, methanol has one active hydrogen atom, ethylene glycol has two, methylamine has two, etc.

From 0.001 mol to 10 mol of 1,3-butadiene are used in the telomerization reaction for every mole of active hydrogen atoms of the telogen which can react with the 1,3-butadiene. When the reaction is carried out using a liquid phase, a ratio of from 0.1 mol to 2 mol of 1,3-butadiene per mole of active hydrogen is preferred.

As telomerization catalysts, it is possible to use homogeneous, heterogeneous or immobilized catalysts or combinations thereof. Many catalysts for this reaction are described in the literature (cf. A. Behr, "Homogeneous Transition Metal Catalysts", Aspects of Homogeneous Catalysis, 1984, 5, 3–73). For example, transition metals of transition group VIII of the Periodic Table of the Elements and their complexes are used successfully as catalysts.

For the purposes of the present invention, the use of nickel, rhodium, palladium and platinum catalysts is preferred. Particular preference is given to using palladium catalysts. It is possible to use either palladium(0) or palladium(II) compounds in the telomerization step. Examples of suitable palladium compounds are palladium(II) chloride, palladium(II) bromide, palladium(II) acetate, palladium(II) formate, palladium(II) octanoate, palladium(II) carbonate, palladium(II) sulfate, palladium(II) nitrate, palladium(II) acetylacetonate, palladium(II) alkyl-sulfonate, $Na_2PdCl_4$, $K_2PdCl_4$, dichlorobis(benzonitrile)palladium, allylpalladium chloride, allylpalladium acetate, trisallylpalladium, 1,5-cyclo-octadienepalladium(II) chloride, bis(triphenylphosphine)palladium(II) chloride, (1,2-bis(diphenylphosphino)ethane)palladium(II) chloride. When using palladium halides, an activator needs to be added to the reaction, since free halide ions inhibit the telomerization reaction. The use of palladium(II) salts having organic anions, e.g. palladium acetate or palladium acetylacetonate, is therefore preferred. Examples of palladium(0) complexes include complexes of palladium with phosphorus, nitrogen or arsenic donor atoms, alkyne, alkene and diene complexes. Examples of phosphorus ligands are phosphines, phosphites, phosphonites or phosphinites, and examples of nitrogen ligands are amines, nitrites and pyridines. Specific examples are tetrakis(triphenylphosphine)palladium(0), tris(dibenzylideneacetone)dipalladium(0) and bis(1,5-cyclooctadiene) palladium.

The amount of telomerization catalyst used depends on its activity. In principle, any amount of catalyst which ensures a sufficient reaction rate can be used. In homogeneously catalyzed reactions in which starting materials, products and a transition metal catalyst are present in solution in a single phase, it is usual to use from 0.1 ppm to 50 000 ppm of metal (based on the reaction mixture). When using palladium catalysts, preference is given to using from 1 ppm to 1 000 ppm, particularly preferably from 3 ppm to 100 ppm, of catalyst metal.

If the telomerization is carried out in multiphase systems (for example heterogeneously catalyzed or two liquid phases of which one comprises the catalyst), these concentration ranges can be different. When the telomerization is carried out in a plurality of liquid phases, it is particularly advantageous for catalyst and product to be present in different phases, since the catalyst can then easily be separated off by means of phase separation. Water often forms one of the liquid phases. However, for example, perfluorinated hydrocarbons, ionic liquids and supercritical carbon dioxide are also used (on the subject of ionic liquids, see P. Wasserscheid, W. Keim, Angew. Chem., Int. Ed. 2000, 39, 3772–3789). The telomerization of butadiene by means of water in ionic liquids is described by J. E. L. Dullius, P. A. Z. Suarez, S. Einloft, R. F. de Souza, J. Dupont, J. Fischer, A. D. Cian, Organometallics 1999, 17, 997–1000. A review of water as carrier phase for the catalyst may be found, for example, in B. Cornils, W. A. Herrmann (Eds.) "Aqueous-Phase Organometallic Catalysis", Wiley-VCH, Weinheim, New-York, Chichester, Brisbane, Singapore, Toronto, 1998. In processes using a plurality of liquid phases, it is particularly advantageous to use a telogen which is present together with the catalyst in one phase while the products are mainly present in a second phase.

The telomerization catalysts can be introduced in active form into the process, but it is often simpler to use a precursor which forms the catalytically active species under the reaction conditions.

The course of the telomerization reaction can generally be improved considerably by addition of ligands to the reaction. It is therefore advantageous to carry out step 1 of the process of the invention in the presence of ligands. Suitable ligands are in principle all those which increase the reaction rate, improve the selectivity of the formation of compound II, increase the working life of the catalyst, etc. Examples of suitable ligands are compounds containing one or more trivalent phosphorus, arsenic, antimony or nitrogen atoms.

Examples of phosphorus ligands are:

phosphines such as triphenylphoshine, tris(p-tolyl)phosphine, tris(m-tolyl)phosphine, tris(o-tolyl)phosphine, tris (p-methoxyphenyl)phosphine, tris(p-di-methylaminophenyl)phosphine, tricyclohexylphosphine, tricyclopentylphosphine, triethylphosphine, tris-(1-naphthyl)phosphine, tribenzylphosphine, tri-n-butyl-phosphine, tri-tert-butylphosphine, tris(3-sulfonato-phenyl) phosphine (metal salt), bis(3-sulfonatophenyl)-phenylphosphine (metal salt), (3-sulfonatophenyl)diphenylphosphine (metal salt);

phosphites such as trimethyl phosphite, triethyl phosphite, tri-n-propyl phosphite, tri-i-propyl phosphite, tri-n-butyl phosphite, tri-i-butyl phosphite, tri-tert-butyl phosphite, tris(2-ethylhexyl) phosphite, triphenyl phosphite, tris(2, 4-di-tert-butyl-phenyl) phosphite, tris(2-tert-butyl-4-methoxyphenyl) phosphite, tris(2-tert-butyl-4-methylphenyl) phosphite, tris(p-cresyl) phosphite;

phosphonites such as methyidiethoxyphosphine, phenyldimethoxyphosphine, phenyldiphenoxyphosphine, 2-phenoxy-2H-dibenz[c,e][1,2]oxaphosphorin and its derivatives in which all or some of the hydrogen atoms are replaced by alkyl and/or aryl radicals or halogen atoms;

phosphinites such as diphenyl(phenoxy)phosphine and its derivatives in which all or some of the hydrogen atoms are replaced by alkyl and/or aryl radicals or halogen atoms, diphenyl(methoxy)phosphine, diphenyl(ethoxy)phosphine, etc.

For the purposes of the present invention, phosphonium salts can also function as ligands. Examples of suitable phosphonium salts and their use in telomerization may be found in, inter alia, EP-A-0 296 550.

When using transition metal catalysts, the ratio of ligand to metal (mol/mol) is normally from 0.1/1 to 500/1, preferably from 0.5/1 to 50/1, particularly preferably from 1/1 to 20/1. The ligand can be added to the reaction as such, in dissolved form or in the form of metal complexes. Additional ligand can be added to the reaction at any point in time and at any location in the reactor as such, as a solution or in the form of a metal complex.

It is often advantageous to carry out the telomerization reaction in the presence of bases. Examples of suitable bases are metal hydroxides, in particular alkali metal hydroxides and alkaline earth metal hydroxides, metal carbonates and metal hydrogencarbonates, in particular alkali metal and alkaline earth metal carbonates and alkali metal and alkaline earth metal hydrogen carbonates, hydroxides of quaternary ammonium or phosphonium ions, alkoxides, enolates, phenoxides, metal salts of carboxylic acids, metal amides such as sodium amide or lithium diethylamide, alkali metal borohydrides, alkali metal aluminum hydrides and organic nitrogen bases, in particular amines such as triethylamine, pyridine or trioctylamine. It is particularly advantageous to use metal salts of the telogen, corresponding to the formula IV.

In this formula, M is a monovalent metal or a fraction depending on the stoichiometry of a polyvalent metal. X and Y are as defined above. M is preferably an alkali metal, alkaline earth metal, boron or aluminum, particularly preferably lithium, sodium or potassium. Compounds of the formula IV can often be obtained easily from the reaction of the telogen of the formula I with the metal. This can also be carried out in situ.

The amount of base added to the telomerization reaction is strongly dependent on the type of base used. When using transition metal catalysts, it is normal to use from 0 to 50 000 mol of base per mole of transition metal, preferably from 0.5 to 5 000 mol, particularly preferably from 0.5 to 500 mol, of base per mole of transition metal. It is also possible to use a plurality of bases at once.

The addition of other auxiliaries can be advantageous for carrying out step 1 of the process of the invention. For example, it may be advantageous to use inhibitors which suppress the polymerization of butadiene. Such inhibitors are normally present in commercial (stabilized) pure 1,3-butadiene. An example of a standard stabilizer is tert-butylcatechol.

Step 1 of the process of the invention can be carried out in the absence of solvents or with addition of solvents. The solvent used should be largely inert. Preference is given to the addition of solvents when telogens which are solid under the reaction conditions are used or in the case of products which would be obtained as solids under the reaction conditions. Suitable solvents include aliphatic, cycloaliphatic and aromatic hydrocarbons, for example $C_3$–$C_{20}$-alkanes, mixtures of lower or higher alkanes ($C_3$–$C_{20}$), cyclohexane, cyclooctane, ethylcyclohexane, alkenes and polyenes, vinylcyclohexene, 1,3,7-octatriene, $C_4$-hydrocarbons from $C_4$ fractions from crackers, benzene, toluene and xylene; polar solvents such as tertiary and secondary alcohols, amides such as acetamide, dimethylacetamide and dimethylformamide, nitriles such as acetonitrile and benzonitrile, ketones such as acetone, methyl isobutyl ketone and diethyl ketone and diethyl ketone, carboxylic esters such as ethyl acetate, ethers such as dipropyl ether, diethyl ether, methyl tert-butyl ether (MTBE), dimethyl ether, methyl octyl ether, 3-methoxyoctane, dioxane, tetrahydrofuran, anisole, alkyl and aryl ethers of ethylene glycol, diethylene glycol and polyethylene glycol and other polar solvents such as sulfolane, dimethyl sulfoxide, ethylene carbonate and propylene carbonate. Water can also be used as solvent. The solvents are used alone or as mixtures of various solvents.

Step 1 of the process of the present invention is advantageously carried out in the absence of oxygen, since oxygen has an adverse effect on the stability of the catalyst systems.

The temperature at which the telomerization reaction is carried out is in the range from 10° C. to 200° C., preferably from 40° C. to 150° C., particularly preferably from 40° C. to 110° C. The reaction pressure is from 1 bar to 300 bar, preferably from 1 bar to 120 bar, particularly preferably from 1 bar to 64 bar and very particularly preferably from 1 bar to 20 bar.

For the purposes of the process of the invention, it is not necessary to achieve complete conversion of the butadiene in the telomerization. The butadiene conversion is from 5% to 100%, preferably from 50% to 100%, particularly preferably from 80% to 100%.

Step 1 of the process of the invention can be carried out continuously or batchwise and is not restricted to the use of particular types of reactor.

Examples of reactors in which the reaction can be carried out are stirred tank reactors, cascades of stirred tanks, flow tubes and loop reactors. Combinations of various reactors are also possible, for example a stirred tank reactor together with a downstream flow tube.

The heat of reaction which is evolved in the reaction is removed by known methods, for example by means of internal or external coolers. Specifically, this may involve the use of shell-and-tube reactors, reactors with cooling fingers, cooling coils or cooling plates or plants which involve cooling of a recycle stream (recirculation reactors, reactors with recycle).

The telomerization catalyst used in step 1 of the process of the invention can be recovered after the telomerization reaction and all or some of it can be used for further telomerization reactions (cf. EP-A-0 218 100). The catalyst can be separated off by, for example, distillation, extraction, precipitation or adsorption. If all or some of the catalyst is present in a second phase, it can be separated off simply by separation of the phases.

It is also possible for the catalyst to be modified prior to being separated off or during the separation. This applies analogously to the total or partial recirculation in the process, which can likewise be preceded by modification of the catalyst. For example, U.S. Pat. No. 4,146,738 describes a process in which the catalyst is stabilized by means of auxiliaries prior to being separated off. After separation from the other products, it is activated and returned to the process.

As an alternative, the catalyst can also be worked up in other ways after the reaction (cf. WO 90/13531, U.S. Pat. No. 5,254,782).

If the telogen used is not reacted completely in step 1, the excess telogen is preferably separated off from the output from step 1 of the process of the invention and all or some of it is returned to step 1.

Step 1 of the process of the invention results in formation of the product of the formula II together with, as by-products, mainly 1,7-octadiene substituted in the 3 position, 1,3,7-octatriene and 4-vinylcyclohexene. Small amounts of relatively high-boiling components are also present. For the further process, it can be advantageous to separate off all or part of the by-product from the product of the formula II. In principle, all methods or combinations of methods by means of which the compound of the formula II can be separated from the product mixture can be employed. The preferred separation technique is distillation. The distillation can be carried out using all available apparatuses and techniques, for example tray columns, packed columns, dividing wall columns, extractive distillation, thin film evaporators and falling film evaporators. The separation by distillation can be carried out in one or more steps and is dependent on the boiling points of the components present in the product mixture. If butadiene-containing mixtures of $C_4$-hydrocarbons are used as feedstocks, the remaining $C_4$-hydrocarbons have the lowest boiling point and can therefore easily be separated off at the top of the distillation apparatus.

When isobutene is present in the remaining $C_4$-hydrocarbons and alcohols are used as telogen, there is the additional possibility of separating off excess alcohol together with the $C_4$-hydrocarbons and reacting them further in other processes. For example, if isobutene is present in the $C_4$-hydrocarbons and methanol is used as telogen, then $C_4$-hydrocarbons remaining after the telomerization can be separated off together with excess methanol and fed together into an MTBE synthesis.

It can also be advantageous to isolate other components of the output from step 1 of the process of the invention and, if appropriate, return them to the process or utilize them separately. As regards the techniques used for this purpose, what has been said in the case of the isolation of the product of the formula II applies analogously. Components which may usefully be isolated are, in particular, the telogen used, excess 1,3-butadiene, the 1,7-octadiene substituted in the 3 position, 1,3,7-octatriene, 4-vinylcyclohexene, the base or bases used and any solvent used.

The product of the formula II is hydrogenated in step 2 to form the product of the formula III. The product of the formula II can be used here in pure form or else in mixtures with one or more of the other components from step 1.

The hydrogenation to form the product of the formula III can be carried out as a liquid-phase or gas-phase hydrogenation or by a combination of these techniques and can be carried out in one or more steps, for example in a preliminary hydrogenation and a final hydrogenation.

The hydrogenation can be carried out continuously or batchwise. Reactors used can be the known standard reactors for hydrogenations, for example trickle bed reactors. The heat of reaction which is evolved in the reaction is removed by known methods, for example by means of internal or external coolers. Specifically, this may involve the use of shell-and-tube reactors, reactors with cooling fingers, cooling coils or cooling plates or plants which involve cooling of a recycle stream (recirculation reactors, reactors with recycle).

The hydrogenation is carried out in the presence of a catalyst. It is possible to use either homogeneous or heterogeneous catalysts. For example, transition metals, in particular copper, chromium and the metals of transition group VIII of the Periodic Table, are used as catalysts for this hydrogenation.

When using homogeneous catalysts, additional ligands can be used together with the catalyst metal. Examples of suitable ligands are compounds of trivalent phosphorus (for example phosphines or phosphites), compounds of trivalent arsenic or antimony, nitrogen compounds (for example amines, pyridines, nitrites), halides, carbon monoxide and cyanide.

In the case of heterogeneous catalysts, the abovementioned metals may be modified with other metals or moderators. Thus, for example the activity and selectivity of heterogeneous palladium catalysts are frequently modified by addition of sulfur or carbon monoxide. A proportion of chromium is frequently added to copper catalysts.

The use of supported catalysts is generally advantageous since smaller amounts of metal are required and the properties of the catalyst can additionally be influenced via the nature of the support. Support materials which have been found to be useful are, for example, activated carbon, aluminum oxide, silicon dioxide, silicon aluminum oxide, barium carbonate, barium sulfate and kieselguhr.

The hydrogenation of the 2,7-octadienyl radical to the 2-octenyl radical is known from the literature. Examples of the homogeneously catalyzed hydrogenation may be found in Chemistry Letters 1977, 1083–1084 and Bull. Chem. Soc. Jap. 1968, 41, 254–255. U.S. Pat. No. 5,118,837 describes the use of heterogeneous catalysts.

The hydrogenations are carried out at temperatures of from 0 to 400° C., preferably from 20 to 200° C. The pressure is in the range from 0.01 to 300 bar, preferably from 0.1 to 125 bar, particularly preferably from 1 to 64 bar.

The hydrogenation in the liquid phase, regardless of whether it is homogeneously or heterogeneously catalyzed, can be carried out in the absence of solvents or in the presence of additional solvents. Examples of suitable solvents are aliphatic and cycloaliphatic hydrocarbons such as $C_3$–$C_{16}$-alkanes, mixtures of lower or higher alkanes ($C_3$–$C_{20}$), cyclohexane, cyclooctane and ethylcyclohexane; alcohols such as methanol, ethanol, propanol, isopropanol, n-butanol, isobutanol, 2-ethylhexanol, isononanol and isotridecanol; polyols such as ethylene glycol, propylene glycol, 1,3-propanediol and 1,4-butanediol; carboxylic esters such as ethyl acetate; ethers such as dipropyl ether, diethyl ether, dimethyl ether, methyl tert-butyl ether, methyl octyl ether, 3-methoxyoctane, dioxane, tetrahydrofuran, alkyl ethers of ethylene glycol, diethylene glycol and polyethylene glycol; sulfolane, dimethyl sulfoxide, ethylene carbonate, propylene carbonate and water. The solvents are used alone or else as mixtures of various solvents.

When the hydrogenation is carried out in the liquid phase, a plurality of liquid phases can be present. This method is particularly advantageous when catalyst and product are present in different phases, since the catalyst can then easily be separated off by phase separation. Water often also forms one of the liquid phases. However, for example, perfluorinated hydrocarbons, ionic liquids and supercritical carbon dioxide are also used (on the subject of ionic liquids, see P. Wasserscheid, W. Keim, Angew. Chem., Int. Ed. 2000, 39, 3772–3789). A review of water as carrier phase for the catalyst may be found, for example, in B. Cornils, W. A. Herrmann (Eds.) "Aqueous-Phase Organometallic Catalysis", Wiley-VCH, Weinheim, New York, Chichester, Brisbane, Singapore, Toronto, 1998.

In the case of hydrogenations in the gas phase, other gases may be present in addition to hydrogen and substrate. For example, nitrogen and/or argon and/or alkanes which are gaseous under the hydrogenation conditions, for example methane, propane or butane, can be added.

Both in gas-phase hydrogenations and in liquid-phase hydrogenations, one or more components from step 1 of the process of the invention can be present in the full or in part. It is possible for these components also to be reduced under the conditions of the hydrogenation. Thus, for example, the 1,7-octadienes substituted in the 3 position which are formed as by-product are at least partly hydrogenated, while the 1,3,7-octatriene is likewise converted at least partly into less unsaturated or saturated species (octadienes, octenes, octane).

The hydrogenation in step 2 of the process of the invention can be carried out continuously, semicontinuously or batchwise. It is preferably carried out continuously.

In step 2 of the process of the invention, a very complete conversion of the compound of the formula II is preferably achieved. However, it is also possible to stop the reaction at a partial conversion and to separate off the unreacted compound II from the remaining components and return it to step 2 or, if desired, utilize it otherwise.

The product of the formula III from step 2 is converted in a third step into 1-octene and further dissociation products. It may be useful to purify the product of the formula III beforehand by physical methods. In principle, it is possible to employ all methods or combinations of methods by means of which the by-products can be completely or partly separated off from the compound of the formula III. The preferred separation technique is distillation. The distillation can be carried out using all available apparatuses and techniques, for example tray columns, packed columns, dividing wall columns, extractive distillation, thin film evaporators and falling film evaporators. The separation by distillation can be carried out in one or more steps and is dependent on the boiling points of the components present in the product mixture.

In step 3 of the process of the invention, the compound of the formula III is dissociated (cracked) to form 1-octene. The further dissociation products are dependent on the telogen used in step 1. For example, when methanol is used as telogen in step 1 of the process of the invention, formaldehyde is formed, while when ethanol is used, acetaldehyde is formed, when n-butanol is used, butanal is formed, and when diethylamine is used, ethylethylidenimine.

The dissociation can be carried out either in the liquid phase or in the gas phase. The dissociation can be carried out in the presence of any amount of other substances which are inert or largely inert under the dissociation conditions. For example, nitrogen or argon or else water, water vapor or alkanes such as methane, propane or butane can be added.

The temperature at which the dissociation of the compound of the formula III is carried out is in the range from 100 to 800° C., preferably from 150 to 600° C., particularly preferably from 250 to 500° C.

The pressure is from 0.05 to 300 bar, preferably from 1 to 125 bar, particularly preferably from 1 to 64 bar.

The dissociation reaction can be carried out in the absence of catalysts or in the presence of heterogeneous catalysts. Preference is given to using catalysts which have Lewis-acid centers, for example amorphous silica-aluminas, aluminas, silicas, silica gels, aluminum-containing silica gels, clay minerals and zeolites.

The dissociation in step 3 of the process of the invention can be carried out continuously, semicontinuously or batchwise.

A further process variant is dissociation of the compound of the formula III with the dissociation products being separated off at the same time. The dissociation products can, for example, be separated off via the gas phase. This can, for example, be achieved technically by means of a distillation; in the lower, hotter part of the distillation, the compound of the formula III is dissociated, while the 1-octene formed and, if appropriate, further dissociation products are separated off at the top.

In the dissociation, all or part of the compound of the formula III is dissociated. In the case of partial conversion, the output from the dissociation still contains unreacted starting material of the formula II. This can, after the 1-octene formed and, if appropriate, other dissociation products have been separated off, be returned to the dissociation. However, it is also possible for only the 1-octene and part of the other dissociation products to be separated off and the recycled stream to be recirculated to the prepurification upstream of the actual dissociation.

The 1-octene is separated from the other components of the output from the dissociation by known methods, for example phase separation, extraction, scrubbing, distillation or precipitation. It is strongly dependent on the telogen used in the telomerization. Thus, the formaldehyde formed in the dissociation of 1-methoxy-2-octene can be separated from the 1-octene simply by extraction with water. If water or water vapor is added in the dissociation of 1-methoxy-2-octene, an aqueous formaldehyde solution is formed in the work-up. In both cases, the organic phase comprising the 1-octene can then be further purified, for example by distillation. On the other hand, if butanol, for example, is used as telogen in the telomerization step, the dissociation of the 1-butoxy-2-octene forms, inter alia, butyraldehyde. In this case, the products of the dissociation can be separated into the individual components by, for example, distillation.

The dissociation of the compound of the formula III forms, in addition to 1-octene, other dissociation products containing unsaturated bonds (double and/or triple bonds) which in the present description are referred to as dissociation products IV. One option according to the present invention is to hydrogenate these dissociation products by means of hydrogen. This hydrogenation can be carried out directly during the dissociation, subsequent to the dissociation or after partial or complete separation of the products from step 3 of the process of the invention. The product of the hydrogenation can, if desired after purification, be used in full or in part as telogen in step 1. For example, if ethanol is used as telogen, step 3 of the process of the invention forms acetaldehyde which is converted by hydrogenation back into ethanol, butanol correspondingly forms butyraldehyde which can be hydrogenated to form butanol again, etc.

The hydrogenation of the dissociation product IV is carried out in one or more stages in the presence of catalysts. The hydrogenation in the individual stages can be carried out in the gas phase or in the liquid phase. It is possible to use homogeneously dissolved catalysts or heterogeneous catalysts. Preference is given to using heterogeneous catalysts. For example, transition metals are used as catalysts for the hydrogenation of the dissociation product IV. Particular mention may be made of copper, chromium and the metals of transition group VIII of the Periodic Table.

In the case of heterogeneous catalysts, the abovementioned metals may be modified with other metals or moderators. For example, a proportion of chromium is often added to copper catalysts.

The use of supported catalysts is generally advantageous, since smaller amounts of metal are required and the properties of the catalyst can additionally be influenced via the nature of the support. Support materials which have been found to be useful are, for example; activated carbon, aluminum oxide, silicon dioxide, silicon aluminum oxide, barium carbonate, barium sulfate and/or kieselguhr.

The hydrogenations of the dissociation products IV are, if they are not carried out under the conditions of the dissociation, carried out at temperatures of from 0 to 400° C., preferably from 50 to 250° C. The pressure is in the range from 0.01 to 300 bar, preferably from 0.1 to 125 bar, particularly preferably form 1 to 64 bar.

Reactors used can be the known standard reactors for hydrogenations, for example trickle bed reactors. The heat of reaction which is evolved in the reaction is removed by known methods, for example by means of internal or external coolers. Specifically, this may involve the use of shell-and-tube reactors, reactors with cooling fingers, cooling coils or cooling plates or plants which involve cooling of a recycle stream (recirculation reactors, reactors with recycle).

If the dissociation of the compounds of the formula III and the hydrogenation of the dissociation products IV are carried out in a single step, the heterogeneous catalysts described above for the respective reactions can be used side by side. It is also possible to use catalysts which catalyze both reactions, for example transition metals on Lewis-acid supports. In this case, the dissociation reaction has to be carried out in the presence of hydrogen.

The hydrogenation in the liquid phase, regardless of whether it is homogeneously or heterogeneously catalyzed, can be carried out in the absence of solvents or in the presence of additional solvents. Examples of suitable solvents are water, aliphatic and cycloaliphatic hydrocarbons such as $C_3$–$C_{16}$-alkanes, mixtures of lower or higher alkanes ($C_3$–$C_{20}$), cyclohexane, cyclooctane and ethylcyclohexane; alcohols such as methanol, ethanol, propanol, isopropanol, n-butanol, isobutanol, 2-ethylhexanol, isononanol and isotridecanol; polyols such as ethylene glycol, propylene glycol, 1,3-propanediol and 1,4-butanediol; carboxylic esters such as ethyl acetate; ethers such as dipropyl ether, diethyl ether, dimethyl ether, methyl tert-butyl ether, methyl octyl ether, 3-methoxyoctane, dioxane, tetrahydrofuran, alkyl ethers of ethylene glycol, diethylene glycol and polyethylene glycol; sulfolane, dimethyl sulfoxide, ethylene carbonate and propylene carbonate. The solvents are used alone or else as mixtures of various solvents.

In the dissociation, small amounts of other $C_8$-olefins can be formed in addition to the 1-octene. Thus, 2-octene can be formed by isomerization of 1-octene, 3-octene can be formed from the 2-octene, etc. Octane and octadiene can also be formed. To achieve a very high 1-octene purity (>97%), it can therefore be necessary to separate off part of these $C_8$ components. This can be carried out by distillation. This distillation can either be carried out together with the separation of other products from the dissociation step (and optionally the hydrogenation products of the dissociation products IV) or can be carried out separately as a purification of a previously isolated $C_8$ fraction.

The following examples illustrate the invention without restricting its scope which is defined in the description and the claims.

EXAMPLES

Example 1

Methanol as Telogen, 1-methoxy-2,7-octadiene

In a 70 l autoclave, 14 kg of methanol, 21 kg of 1,3-butadiene, 7.5 g of palladium(II) acetate, 85 g of triphenylphosphine and 160 g of triethylamine were heated to 80° C. in the absence of water and oxygen. A pressure rise to 8 bar was observed. Under these conditions, the reaction started. The pressure decreased again with the commencement of the reaction of 1,3-butadiene. After 24 hours, the autoclave was cooled to room temperature and the remaining pressure was released. According to GC analysis, 98% of the 1,3-butadiene had reacted. The main products obtained were:

| Component | CAS No. | Proportion in % |
|---|---|---|
| Methanol | 64-56-1 | 32.3 |
| 1,3,7-Octatriene | 1002-35-3 | 9.3 |
| 4-Vinylcyclohexene | 100-40-3 | 0.2 |
| 3-Methoxy-1,7-octadiene | 20202-62-4 | 7.8 |
| 1-Methoxy-2,7-octadiene | 14543-49-8 | 48.8 |
| Others | | 1.6 |

To work up the output from the reactor, it was subjected to a batch distillation at 80 mbar to separate it into a catalyst residue and a distillate.

Example 2

Homogeneously Catalyzed Hydrogenation 1000 g of 1-methoxy-2,7-octadiene, 500 ml of tetrahydrofuran, 500 ml of ethanol and 2.5 g of tris(triphenylphosphine)ruthenium(II) chloride were placed in a 3 l Büchi autoclave. The temperature was set to 30° C. and the autoclave was pressurized to 30 bar by means of hydrogen. The reaction was followed via the amount of hydrogen taken up and by means of GC analyses. After 6 hours, the reaction was stopped. According to GC analysis, 98% of the 1-methoxy-2,7-octadiene had reacted to form 1-methoxy-2-octene (cis and trans) with a selectivity of 89%. The 1-methoxy-2-octene was separated from solvents and catalyst by distillation.

Example 3

Heterogeneously Catalyzed Hydrogenation

A gradient-free differential circulation reactor from Xytel was charged with 15 g of a heterogeneous ruthenium catalyst. To immobilize the catalyst, it was located in a small wire mesh basket. The proportion by weight of ruthenium on the support material $\lambda$-$Al_2O_3$ was 1% by weight. Before commencement of the reaction, the catalyst was reduced in a hydrogen atmosphere at 200° C. After the reduction, 900 ml of a mixture of trans-1-methoxy-2,7-octadiene and cis-1-methoxy-2,7-octadiene in a mass ratio of 96:4 were introduced into the differential circulation reactor. The reaction mixture was hydrogenated under batch conditions at a hydrogen partial pressure of 10 bar. According to GC analysis, the progress of the reaction at 40° C. was as follows:

| $LHSV^{-1}$ kg h/ltr | cis-MOE % by wt | trans-MOE % by wt | cis-MODE % by wt | trans-MODE % by wt | Others % by wt |
| --- | --- | --- | --- | --- | --- |
| 0.0083 | 0.13 | 1.33 | 6.25 | 91.25 | 1.04 |
| 0.0167 | 0.13 | 1.99 | 6.16 | 09.33 | 1.38 |
| 0.0250 | 0.18 | 3.05 | 6.20 | 88.40 | 2.17 |
| 0.0333 | 0.23 | 4.11 | 6.01 | 87.97 | 1.68 |
| 0.0417 | 0.33 | 5.57 | 5.95 | 86.12 | 2.04 |
| 0.0500 | 0.40 | 6.80 | 5.77 | 85.04 | 1.99 |
| 0.0667 | 0.50 | 8.71 | 5.60 | 82.11 | 3.08 |
| 0.0833 | 0.64 | 11.17 | 5.45 | 80.26 | 2.48 |
| 0.1083 | 0.81 | 13.87 | 5.24 | 77.39 | 2.69 |
| 0.1333 | 1.00 | 16.95 | 4.97 | 74.02 | 3.05 |
| 0.1583 | 1.18 | 19.87 | 4.74 | 70.87 | 3.35 |
| 0.3750 | 2.98 | 52.01 | 2.24 | 36.08 | 6.69 |
| 0.4000 | 3.26 | 57.11 | 1.86 | 30.09 | 7.69 |
| 0.4250 | 3.48 | 61.01 | 1.59 | 25.52 | 8.40 |
| 0.4500 | 3.67 | 65.01 | 1.28 | 21.55 | 8.49 |
| 0.4917 | 4.03 | 73.13 | 0.80 | 13.47 | 9.58 |
| 0.5250 | 4.20 | 76.2 | 0.54 | 8.67 | 10.39 |

(cis-MOE = cis-1-methoxy-2-octene, trans-MOE = trans-1-methoxy-2-octene, cis-MODE = cis-1-methoxy-2,7-octadiene, trans-MODE = trans-1-methoxy-2,7-octadiene)

The above-described trial was repeated at 50° C. under otherwise identical experimental conditions. As expected, the reaction rate increased with temperature. According to GC analysis, the progress of the reaction at 50° C. was as follows:

| $LHSV^{-1}$ kg h/ltr | cis-MOE % by wt | trans-MOE % by wt | cis-MODE % by wt | trans-MODE % by wt | Others % by wt |
| --- | --- | --- | --- | --- | --- |
| 0.0083 | 0.12 | 2.77 | 3.80 | 90.33 | 2.99 |
| 0.0167 | 0.16 | 4.16 | 3.77 | 89.14 | 2.76 |
| 0.0250 | 0.23 | 6.01 | 3.71 | 87.20 | 2.85 |
| 0.0333 | 0.31 | 7.83 | 3.64 | 84.24 | 3.98 |
| 0.0417 | .036 | 9.01 | 3.63 | 83.13 | 3.87 |
| 0.0583 | 0.48 | 11.84 | 3.55 | 79.63 | 4.50 |
| 0.0917 | 0.70 | 17.08 | 3.31 | 73.20 | 5.70 |
| 0.1167 | 0.88 | 21.37 | 3.16 | 68.21 | 6.38 |
| 0.3667 | 3.06 | 64.30 | 1.09 | 17.87 | 13.68 |
| 0.3833 | 3.28 | 67.72 | 0.88 | 13.97 | 14.15 |
| 0.4000 | 3.44 | 70.27 | 0.72 | 10.82 | 14.75 |
| 0.4167 | 3.59 | 71.53 | 0.71 | 8.01 | 16.16 |
| 0.4333 | 1.28 | 74.29 | 0.44 | 5.52 | 18.48 |
| 0.4667 | 3.91 | 75.77 | 0.30 | 1.51 | 18.51 |

Example 4

Dissociation to Give 1-octene

A gaseous mixture of 1-methoxy-2-octene (cis and trans) [CAS 60171-33-7] and nitrogen was fed continuously into a 100 ml gradient-free differential circulation reactor. The total amount fed in was 60 standard ml/min. The proportion of inert gas in the feed was 83%. The dissociation of 1-methoxy-2-octene into 1-octene and formaldehyde was carried out under atmospheric pressure in a temperature range of 375–450° C. Based on the 1-methoxy-2-octene in the feed gas, the following conversions of 1-methoxy-2-octene and selectivities to 1-octene were observed at a residence time of 40 s:

| Temperature [° C.] | 375 | 400 | 425 |
| --- | --- | --- | --- |
| Conversion of methyl 2-octenyl ether [%] | 4.83 | 16.7 | 36.7 |
| Selectivity of formation of 1-octene [%] | 89.7 | 77.7 | 75.7 |

The invention claimed is:

1. A process for preparing 1-octene, which comprises:
   (I) reacting 1,3-butadiene with a telogen of the formula H—X—Y—H, where X is O, N, S or P and Y is C, N, or Si and X and Y bear, depending on their valence, further substituents, in the presence of a telomerization catalyst to form a telomer of the formula:

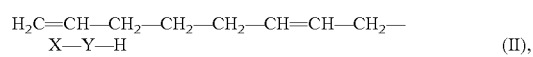

(II) hydrogenating the telomere to form a 1-substituted 2-octene of the formula:

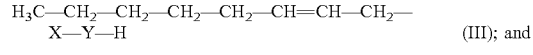

(III) dissociating the 1-substituted 2-octene to give 1-octene and other dissociation products (IV).

2. The process for preparing 1-octene as claimed in claim 1, wherein the substituents on X and/or Y are hydrogen, alkyl radicals having 1–50 carbon atoms, aryl radicals having 6–50 carbon atoms and/or heteroaryl radicals, where the substituents are identical or different and may in turn be substituted by the groups alkyl, aryl, —F, —Cl, —Br, —I, —$CF_3$, —OR, —COR, —$CO_2$R, —OCOR, —SR, —$SO_2$R, —SOR, —$SO_3$R, —$SO_2NR_2$, —$NR_2$, —N=$R_2$, —$NH_2$ where R=H or a substituted or unsubstituted, aliphatic or aromatic hydrocarbon radical having from 1 to 25 carbon atoms.

3. The process for preparing 1-octene as claimed in claim 1, wherein the telogen comprises a compound selected from the group consisting of a monoalcohol, a dialcohol, a primary amine and a secondary amine.

4. The process for preparing 1-octene as claimed in claim 3, wherein the telogen comprises a compound selected from the group consisting of methanol, ethanol, n-propanol, isopropanol, allyl alcohol, n-butanol, i-butanol, octanol, 2-ethylhexanol, isononanol, benzyl alcohol, cyclohexanol, cyclopentanol, 2,7-octadien-1-ol, ethylene glycol, 1,2-propanediol, 1,3-propanediol, 1,4-butanediol, 1,2-butanediol, 2,3-butanediol, 1,3-butanediol and an α-hydroxyacetic ester.

5. The process for preparing 1-octene as claimed in claim 3, wherein the telogen comprises a compound selected from the group consisting of methylamine, ethylamine, propylamine, butylamine, octylamine, 2,7-octadienylamine, dodecylamine, ethylenediamine, hexamethylenediamine, dimethylamine, diethylamine, N-methylaniline, bis(2,7-octadienyl)amine, dicyclohexylamine, methylcyclohexylamine, pyrrolidine, piperidine, morpholine, piperazine and hexamethylenimine.

6. The process for preparing 1-octene as claimed in claim 1, wherein from 0.001 mol to 10 mol of 1,3-butadiene is reacted in step (I) for every mole of active hydrogen atom reacted in said hydrogenation step.

7. The process for preparing 1-octene as claimed in claim 1, wherein telogen which has not reacted in step (I) is recovered and returned to step (I).

8. The process for preparing 1-octene as claimed in claim 1, wherein telomerization catalyst of step (I) comprises a transition metal of transition group VIII of the Periodic Table.

9. The process for preparing 1-octene as claimed in claim 8, wherein the transition metal is palladium.

10. The process for preparing 1-octene as claimed in claim 1, wherein telomerization catalyst comprises a catalyst metal and a ligand, and the ligand is a compound comprising a trivalent phosphorus, arsenic, antimony or nitrogen atom.

11. The process for preparing 1-octene as claimed in claim 10, wherein the ligand comprises a compound selected from the group consisting of a phosphine, phosphite, phosphonite and a phosphinite.

12. The process for preparing 1-octene as claimed in claim 10, further comprising adding a base in step (I).

13. The process for preparing 1-octene as claimed in claim 1, wherein the telomerization catalyst of step (I) is recovered and returned in full or in part to the process.

14. The process for preparing 1-octene as claimed in claim 1, wherein the telomerization catalyst of step (I) is not returned to step (I).

15. The process for preparing 1-octene as claimed in claim 1, wherein said hydrogenation is carried out in the presence of hydrogen and a homogeneous hydrogenation catalyst in step (II).

16. The process for preparing 1-octene as claimed in claim 1, wherein said hydrogenation is carried out in the presence of hydrogen and a heterogeneous hydrogenation catalyst in step (II).

17. The process for preparing 1-octene as claimed in claim 15, wherein the hydrogenation catalyst comprises copper, chromium and/or a transition metal of transition group VIII of the Periodic Table in step (II).

18. The process for preparing 1-octene as claimed in claim 1, wherein 1,3,7-octatriene is formed as by-product in step (I) and all or part of the 1,3,7-octatriene is hydrogenated in step (II).

19. The process for preparing 1-octene as claimed in claim 1, wherein 1,3,7-octatriene substituted in the 3 position obtained as a by-product in step (I) and all or part of the 1,3,7-octatriene substituted in the 3 position is hydrogenated in step (II).

20. The process for preparing 1-octene as claimed in claim 1, wherein the dissociation in step (III) is carried out at temperatures in the range from 150° C. to 600° C.

21. The process for preparing 1-octene as claimed in claim 1, wherein less than 5% of $C_8$-hydrocarbons are present in the feed to the dissociation in step (III).

22. The process for preparing 1-octene as claimed in claim 1, wherein the 2-octene substituted in the 1-position is only partly converted in step (III).

23. The process for preparing 1-octene as claimed in claim 1, wherein the unreacted 2-octene substituted in the 1-position separated off from the remaining components of the output from step (III) and is recirculated in full or in part to step (III).

24. The process for preparing 1-octene as claimed in claim 1, wherein the 2-octene substituted in the 1-position is recirculated to a purification step which precedes step (II).

25. The process for preparing 1-octene as claimed in claim 1, wherein, in step (III), the dissociation to give 1-octene is carried out simultaneously with separation of the 1-octene and the products of dissociation formed from starting materials.

26. The process for preparing 1-octene as claimed in claim 1, wherein the dissociation in step (III) is carried out in the presence of water or water vapor.

27. The process for preparing 1-octene as claimed in claim 1, wherein the dissociation in step (III) is carried out in the presence of catalysts.

28. The process for preparing 1-octene as claimed in claim 16, wherein the hydrogenation catalyst comprises copper, chromium and/or a transition metal of transition group VIII of the Periodic Table in step (II).

29. The process for preparing 1-octene as claimed in claim 1, wherein the products of dissociation (IV) other than 1-octene are hydrogenated by hydrogen during dissociation step (III).

30. The process for preparing 1-octene as claimed in claim 1, wherein the products of dissociation (IV) other than 1-octene are hydrogenated by hydrogen subsequent to dissociation step (III).

31. The process for preparing 1-octene as claimed in claim 1, wherein the products of dissociation (IV) other than 1-octene are hydrogenated by hydrogen after partial or complete separation of the products of dissociation from step (III).

* * * * *